United States Patent [19]

Rock et al.

[11] 4,239,508

[45] Dec. 16, 1980

[54] CUMENE RECOVERY

[75] Inventors: Steven L. Rock, Doylestown, Pa.; James S. Clovis, Mougins, France

[73] Assignee: Rohm and Haas Company, Philadelphia, Pa.

[21] Appl. No.: 45,714

[22] Filed: Jun. 5, 1979

[51] Int. Cl.$^3$ ............................................. B01D 53/04
[52] U.S. Cl. ............................................. 55/59; 55/74
[58] Field of Search ...................................... 55/59, 74

[56] References Cited

U.S. PATENT DOCUMENTS

| 3,357,158 | 12/1967 | Hollis | 55/67 |
|---|---|---|---|
| 3,531,463 | 9/1970 | Gustafson | 210/30 R X |
| 3,547,684 | 12/1970 | Hollis et al. | 55/67 X |
| 3,686,827 | 8/1972 | Haigh et al. | 55/74 |
| 3,727,379 | 4/1973 | Bijleveld et al. | 55/74 X |
| 3,798,876 | 3/1974 | Kennedy | 55/74 X |
| 3,805,493 | 4/1974 | Kennedy et al. | 55/74 |
| 4,063,912 | 12/1977 | Neely et al. | 55/74 |
| 4,102,647 | 7/1978 | Roelse et al. | 55/74 X |

Primary Examiner—Robert H. Spitzer
Attorney, Agent, or Firm—Jordan J. Driks

[57] ABSTRACT

A method for removing cumene vapor from a cumene-containing vapor stream comprises passing the vapor stream through a bed of a substantially dry hydrophobic, macroreticular, water-insoluble, crosslinked polymer containing from 20% to 100% by weight of the polymer, of divinylbenzene or a copolymer of divinylbenzene, the balance being ethylvinylbenzene or styrene or mixtures thereof but not more than 50% of either ethylvinylbenzene or styrene, until the capacity of the polymer or copolymer to remove cumene is substantially exhausted. Thereafter, the cumene is desorbed from the mass or bed of the polymer or copolymer by passing steam through said mass or bed. Without drying, the mass or bed is then ready for reuse.

10 Claims, No Drawings

CUMENE RECOVERY

BACKGROUND OF THE INVENTION

This invention relates to the recovery of cumene vapors from a vapor stream containing cumene. More particularly, this invention relates to the recovery of cumene from a cumene containing vapor stream using a polymeric adsorbent which is hydrophobic and requires no drying step after steam desorption of the cumene from the substantially exhausted resin.

Phenol is produced commercially by the oxidation of cumene to cumene hydroperoxide followed by the acid hydrolysis of the cumene hydroperoxide to yield phenol. The waste vapor stream which is produced contains unreacted cumene. If desired, in order to recover the unreacted cumene, the vapor waste stream is passed through a vent condenser to remove the bulk of the cumene from the vapor stream. However, substantial amounts of unreacted cumene are not removed by the vent condenser, if used. These substantial amounts of unreacted cumene would, if not removed and prevented from discharging into the atmosphere, present an environmental problem and would result in the loss of valuable starting material for the preparation of phenol.

One method for recovering unreacted cumene from the off gases involves passing the off gases through a bed of activated carbon. The use of activated carbon to remove cumene has not been satisfactory due to the high operating costs associated with the use of activated carbon and resulting from the necessity for frequent rebedding of the carbon. In addition, activated carbon requires excessive amounts of steam in order to regenerate the exhausted activated carbon bed for reuse. Further, during commercial use, activated carbon beds are subject to the attrition of carbon so that adsorbent is lost as a result of this attrition. Moreover, the use of a bed of activated carbon to remove cumene is not efficient due to the fouling of the activated carbon during repeated operation. An additional disadvantage of using activated carbon is that the capacity of activated carbon to adsorb cumene is adversely affected by the presence of moisture so that, after cumene has been desorbed from the activated carbon by the use of steam, the carbon must be dried prior to reuse and, if not dried, the capacity of the activated carbon to again remove cumene, is adversely affected.

U.S. Pat. No. 3,357,158 is directed to the use of certain microporous polymers for making chromatographic separations. This patent discloses the use of a copolymer of divinylbenzene and ethylvinylbenzene for such chromatographic separations. Example 1 of this patent teaches the preparation of a copolymer of divinylbenzene, ethylvinylbenzene and diethylbenzene wherein the copolymer is dried and has a surface area of 700 square meters per gram. The patent, however, relates only to microporous polymers and does not relate to cumene recovery or to steam regeneration of a macroreticular resin.

U.S. Pat. No. 3,805,493 teaches the use of a copolymer of divinylbenzene and ethylvinylbenzene for the removal of vaporous hydrocarbons, for example from motor vehicle fuel tanks and carburators. This patent fails to teach the removal of cumene vapors from a vapor stream containing the same and further fails to teach that a pre-dried polymer of divinylbenzene and ethylvinylbenzene would be useable without a drying step after the desorption of cumene and subsequent reuse to adsorb cumene.

U.S. Pat. No. 3,531,463 teaches the preparation of a divinylbenzene/ethylvinylbenzene polymer and its use as an adsorbent. This patent, however, is not directed to the use of the adsorbent to recover cumene and further fails to teach the utility of a predried divinylbenzene/ethylvinylbenzene copolymer in cumene recovery.

U.S. Pat. No. 4,063,912 is directed to gaseous phase adsorption using partially pyrolyzed polymer particles. This patent discloses the use of partially pyrolyzed macroporous resins for cumene recovery. The patent shows the superiority of the partially pyrolyzed polymer particles to adsorb phenol when compared with a commercial adsorbent. This patent fails to teach that a divinylbenzene/ethylvinylbenzene/styrene polymer which has been predried would be effective in adsorbing cumene, and that, after desorption of the cumene with the steam, the polymer may be used without first drying the polymer.

U.S. Pat. No. 3,798,876 is directed to the abatement of air pollution from organic compounds using polymeric adsorbents. One of the polymeric adsorbents which is used is a copolymer of divinylbenzene and ethylvinylbenzene. This patent also teaches that after regeneration of the resin with steam, the resin is then dried by the sufficient passage of warm air. This patent also teaches that the copolymer of divinylbenzene and ethylvinylbenzene, under the conditions set forth in the patent, is not as effective as activated carbon in removing toluene, a homolog of cumene (column 5, table 4).

It is an object of this invention therefore, to provide a process for the removal of cumene from a cumene-containing vapor stream.

Another object of this invention is to provide a process for such removal of cumene wherein the adsorbent used may be regenerated with steam and may then by reused without the necessity for drying the adsorbent.

Other objects and advantages will become apparent from the following more complete description and claims.

DETAILED DESCRIPTION

Broadly, this invention contemplates a process for removing cumene vapors from a cumene containing vapor stream which comprises the steps of passing said vapor stream through a mass or bed of substantially dry hydrophobic, macroreticular, water insoluble, cross-linked polymer of from about 20% to 100%, by weight of the polymer, of divinylbenzene, the balance being ethylvinylbenzene or styrene or mixtures thereof but not more than 50% of either ethylvinylbenzene or styrene, until the capacity of the polymer to remove cumene is substantially exhausted, desorbing said cumene from said mass or bed of said polymer by passing steam through said mass or bed and again passing a cumene containing vapor stream through the wet mass or bed of polymer.

The term "polymer" or "polymeric adsorbent" as used hereinafter, means both the polymer and copolymer hereinafter defined.

It has been surprisingly and unexpectedly found that when a divinylbenzene polymer or a copolymer as defined herein, is dried, the dried polymer is useful for adsorbing cumene from a cumene-containing vapor stream and, after regeneration of the polymer with steam, the polymer may again be used for adsorbing cumene without the necessity for first drying the polymer.

The polymers which are useful in practicing this invention are divinylbenzene polymers and copolymers of divinylbenzene with up to about 50% of ethylvinylbenzene or styrene by weight of the polymer and up to about 80% by weight of the polymer of mixtures of ethylvinylbenzene and styrene. If more than 50% of ethylvinylbenzene or of styrene is present, then the copolymer will not have a sufficient surface area to be used efficaciously in practicing this invention.

When ethylvinylbenzene is present, it is preferred to utilize a polymer, as aforesaid, which contains from about 5% to about 25% by weight of ethylvinylbenzene based on the total weight of the polymer composition, and more preferably, from about 5% to about 20% by weight of ethylvinylbenzene.

When styrene is present, it is preferred to utilize a polymer which contains from about 5% to about 15% of styrene by weight of the polymer composition.

The polymer or copolymer should have a surface area of at least about 100 square meters per gram of polymer and preferably from about 500 square meters to about 1,000 square meters. If the polymer has a surface area of less than 100 square meters per gram of polymer, then such surface area will be insufficient to efficaciously remove cumene from a cumene vapor stream.

The macroreticular resins employed herein may be prepared in any suitable manner such as by suspension polymerization of the monomer or comonomers using a precipitating solvent in the monomer phase. Such methods of preparation are well known in the art.

After the polymer or copolymer beads have been prepared, they are then washed with methanol or other suitable solvent to remove soluble organics. Alternatively, soluble organics may be removed by a stream stripping procedure. Thereafter, if the soluble organics have been removed by washing with a suitable solvent, the polymer or copolymer beads are then washed with water or steam stripped to remove the methanol or other solvent which has been used.

At this point, in order for the polymer beads to be useful in practicing this invention, they must then be dried. The term "substantially dry" or "dried" as used in the specification and claims in referring to the polymer or copolymer beads means that the virgin polymer or copolymer beads contain less than about 25% of water, based on the total weight of the polymer beads plus water and preferably less than about 15% of water, as aforesaid.

The drying of the polymer or copolymer beads may be accomplished by heating the beads at a temperature of from about 70° C. to about 110° C. for a period of time of from about 8 to about 24 hours until the water has been driven off. Unless the water has been driven off, the resultant polymer beads will not efficaciously remove cumene from a cumene containing vapor stream.

It is particularly preferred that drying be accomplished at a temperature of 85° C. for a period of about 10 to about 12 hours for economic considerations.

After the capacity of the polymer to adsorb cumene is substantially exhausted, the cumene may be desorbed from the polymer beads by steam stripping the cumene from the polymer or by washing the cumene loaded polymer beads with liquid or vaporized acetone, or other suitable solvent for cumene, followed by steam stripping of the residual acetone from the polymer beads.

It is considered however, that steam desorption, as described herein, also includes the solvent desorption of cumene followed by steam stripping of the solvent as well as steam desorption alone.

Generally, the amount of steam used for steam desorption of cumene will be roughly equivalent to the amount of steam used to remove the residual solvent used for cumene desorption, and still remaining on the polymer beads.

The amount of steam used to desorb the cumene from the polymer beads may vary widely from about 3 pounds of steam per pound of cumene desorbed to about 13 pounds of steam. It is preferred, however, for economic considerations, to utilize between about 3 to about 7 pounds of steam per pound of cumene desorbed from the polymer beads.

It should be understood however that the amount of steam used to desorb cumene from the polymer beads will also be dependent upon the amount of cumene present in the cumene-containing vapor stream and the amount of cumene adsorbed by the bed of polymer beads. The greater the concentration of cumene in the vapor stream, the greater will be the amount of cumene adsorbed by the bed of polymer beads and desorption of the higher concentrations of cumene from the polymer bed will be accomplished with lesser amounts of steam than the amount of steam required for a lesser concentration of cumene on the bed of polymer beads.

The process described herein may be practiced utilizing a single adsorbent bed or two or more adsorbent beds. If more than one adsorbent bed is used, then while one adsorbent bed is being regenerated by steam stripping the cumene therefrom, the other adsorbent bed or beds may be used to treat a cumene containing vapor stream.

A typical commercial cumene recovery operation may utilize two adsorbent beds, each bed containing approximately 1600 pounds of a divinylbenzene/ethylvinylbenzene copolymer; or divinylbenzene/ethylvinylbenzene/styrene terpolymer. The cumene containing vapor waste stream from a phenol plant reactor would either be treated directly upon leaving the reactor or would be treated after having first been passed through a vent condenser to partially reduce the cumene concentration. A typical waste vapor stream emanating from a phenol plant reactor would contain air flowing at the rate of 62,000 pounds per hour; cumene flowing at the rate of 520 pounds per hour; and water vapor flowing at the rate of 350 pounds per hour, all at 90 psia and 32° C. The cumene concentration at the rate set forth above would be, by volume, 2,000 parts per million. The loading cycle consists of passing the pressurized waste vapor stream through the first bed while monitoring the exiting stream for cumene concentration using a suitable hydrocarbon analyzer, gas chromatograph or infrared spectrometer. The cumene concentration of the effluent will typically be less than 2 parts per million before the operating capacity of the adsorbent is exceeded (breakthrough). When the cumene concentration of the effluent from the adsorbent bed steadily increases above 2 parts per million, the adsorbent breakthrough capacity has been reached and the waste vapor stream is then switched to the second adsorbent bed to begin a new loading cycle. Each loading cycle will take place over a period of at least 1 hour. This will correspond to a breakthrough operating capacity of at least 32% (weight of adsorbed cumene divided by adsorbent weight). When the waste vapor stream is switched to the second bed, regeneration of the first bed is commenced by passing low pressure steam through the bed to achieve a temperature, within the bed, of at least 105° C. In this manner, cumene is desorbed from the first bed and the cumene vapor/steam mixture is then sent to a chilled condenser and the condensed cumene/water mixture is passed into a separator where the cumene is recovered. A typical desorption operation, for the adsorbent beds described herein, would require approximately 1700 pounds of steam to recover the 520 pounds of cumene which had been adsorbed during the loading cycle. The time required for regeneration, in the example set forth above, is a maximum of 1 hour. Following regeneration, the first bed is then ready for the next loading cycle without the necessity for drying the first bed.

In order to more fully illustrate the nature of this invention and the manner of practicing the same, the following examples are presented.

EXAMPLES 1 through 12

Experimental Procedure

Between about 0.1 and about 0.4 grams of dry adsorbent is charged to a 250 milliliter round bottom flask equipped with a side arm. The main neck of the flask is sealed with a glass stopper and the side arm is covered with a rubber septum. A given volume of liquid cumene is injected into the flask through the septum using a micro-syringe. Care is taken not to inject the liquid in direct contact with the adsorbent particles. The amount of cumene injected is small enough such that all the cumene liquid will vaporize due to the equilibrium concentration being below the vapor pressure at the test temperature of 21° C. The flask is placed on a shaker apparatus for at least 2 hours to allow equilibrium adsorption to occur. After equilibrium, a 100 microliter gaseous sample is withdrawn from the flask and injected into a flame ionization detector gas chromatograph. The chromatogram peak height is measured and is compared to appropriately prepared gaseous standards to determine the final concentration of the cumene in the vapor. By knowing the initial amount of cumene injected and the final equilibrium concentration, the amount of cumene adsorbed is calculated. The weight of the cumene adsorbed is divided by the weight of adsorbent to obtain the adsorbent saturation capacity at the final vapor concentration.

Table I sets forth the results obtained. The following abbreviations have been used in the table set forth below:

DVB for divinylbenzene; EVB for ethylvinylbenzene; and STY for styrene.

TABLE I

| Sample No. | Polymer Composition (% by Weight) | | | Weight of Adsorbent (grams) | Volume of Cumene Liquid Injected (microliters) | Final Vapor Concentration of Cumene (ppm) | Adsorbent Capacity (milligrams of cumene adsorbed ÷ grams of Adsorbent Present) |
|---|---|---|---|---|---|---|---|
| | DVB | EVB | STY | | | | |
| 1 | 50 | 41 | 9 | 0.1295 | 15 | 150 | 99 |
| 2 | 50 | 41 | 9 | 0.1295 | 45 | 1498 | 279 |
| 3 | 50 | 39 | 11 | 0.3140 | 25 | 150 | 68 |
| 4 | 50 | 39 | 11 | 0.3140 | 50 | 895 | 134 |
| 5 | 50 | 39 | 11 | 0.3140 | 100 | 4193 | 258 |
| 6 | 85 | 15 | — | 0.4133 | 15 | 3 | 31 |
| 7 | 85 | 15 | — | 0.3252 | 75 | 340 | 198 |
| 8 | 85 | 15 | — | 0.3252 | 175 | 1770 | 458 |
| 9 | 29 | 25 | 46 | 0.2509 | 25 | 1060 | 78 |
| 10 | 29 | 25 | 46 | 0.2509 | 60 | 2628 | 189 |
| 11 | 28 | 22 | 50 | 0.2347 | 35 | 1372 | 118 |
| 12 | 28 | 22 | 50 | 0.2347 | 60 | 4410 | 192 |

EXAMPLE 13

The following example compares the steam regeneration efficiency for Witco activated carbon No. 256 and a divinylbenzene (80%) ethylvinylbenzene (20%) copolymer. The bed volume of the resin and of the carbon is 350 cc. The influent stream contains 1900 parts per million of cumene at 4 psig. The steam flow rate is 3.2 to 4.4 cc per minute of condensate. The regeneration temperature is 105° C.

Four cycles are run to achieve equilibrium. A cycle consists of loading the adsorbent with cumene until breakthrough occurs and thereafter regenerating with steam. The average activated carbon bed weight loading is 18.7% and the average divinylbenzene/ethylvinylbenzene copolymer bed weight loading is 35.8%. Bed weight loading is the weight of cumene adsorbed divided by the weight of adsorbent present. The results are presented below.

TABLE 1

Comparison of Steam Regeneration Efficiency for Witco Activated Carbon 256 and Divinylbenzene/Ethylvinylbenzene Copolymer

| Percent Recovery of Cumene | Steam Usage (Pounds Steam Divided by Pounds of Cumene Recovered) | | Carbon Steam Usage Divided by Divinylbenzene/Ethylvinylbenzene Copolymer Steam Usage |
|---|---|---|---|
| | Divinylbenzene/Ethylvinylbenzene Copolymer | Witco Activated Carbon 256 | |
| 100 | 11.6 | 27.8 | 2.4 |
| 95 | 6.4 | 23.6 | 3.7 |
| 90 | 5.0 | 20.5 | 4.1 |
| 80 | 3.8 | 15.2 | 4.0 |
| 70 | 3.7 | 11.7 | 3.2 |

EXAMPLE 14

An insulated, jacketed metal column is loaded with 300 cc of a dried polymeric adsorbent which is 85% divinylbenzene and 15% ethylvinylbenzene. A second jacketed metal column is loaded with 300 cc of dried Witco Activated Carbon 256. The adsorbents of both columns are held in place by metal screens located at both ends of each column. The influent passed through each of the columns is composed of cumene vapor, air and moisture. The air flow is adjusted so that the relative humidity of the cumene vapor containing stream is 95% and the stream temperature is 21° C. The influent pressure is 17 psig and the loading flow rate is 58 bed volumes per minute. The cumene concentration of the vapor stream varies, during the various cycles, from 1200 ppm. to 2200 ppm. For cycle 93, the influent vapor concentration is 1570 ppm. for the vapor stream passing through the polymeric adsorbent and the breakthrough capacity is 219 mg. of cumene per gram of adsorbent. For cycle 96, the influent cumene vapor concentration passing through the activated carbon bed is 1400 ppm. and the breakthrough capacity is 125 mg. of cumene per gram of activated carbon.

The breakthrough capacity for the virgin adsorbents are 334 milligrams of cumene per gram of polymeric adsorbent and 459 milligrams of cumene per gram of activated carbon. A cycle constitutes one loading step and one steam regeneration step. Each column is operated for in excess of 100 cycles. For cycles 70 through 113, steam regeneration is accomplished by passing from 3 to 5 cc of steam condensate per minute through each of the columns for a period of 60 minutes. After each steam regeneration, neither the activated carbon adsorbent or the polymeric adsorbent is dried prior to reloading.

At the end of the 93rd cycle, the column containing the polymeric adsorbent is operating at 66% of its original capacity whereas, after the 96th cycle, the column containing the activated carbon is operating at only 27% of its original capacity.

We claim:

1. A process for removing cumene vapors from a cumene containing vapor stream comprising the steps of passing said vapor stream through a mass or bed of a substantially dry, hydrophobic, macroreticular, water insoluble, cross-linked polymer consisting essentially of from about 20% to 100% by weight of divinylbenzene, the balance being ethylvinylbenzene or styrene or mixtures thereof but not more than 50% of either ethylvinylbenzene or styrene, until the capacity of the polymer to remove cumene is substantially exhausted, desorbing said cumene from said mass or bed of said polymer by passing steam through said mass or bed and again passing a cumene containing vapor stream through the wet mass or bed of polymer.

2. A process according to claim 1 wherein said polymer contains up to about 25% by weight of ethylvinylbenzene, based on the total weight of the polymer.

3. A process according to claim 1 wherein said polymer has a surface area of at least about 100 square meters per gram of polymer.

4. A process according to claim 1 wherein said polymer has a surface area of from about 500 square meters per gram of polymer to about 1000 square meters per gram of polymer.

5. A process according to claim 1 wherein said polymer is a polymer of divinylbenzene and styrene.

6. A process according to claim 1 wherein said polymer is a polymer of styrene, divinylbenzene and ethylvinylbenzene.

7. A process according to claim 1 wherein said polymer is a polymer of divinylbenzene and ethylvinylbenzene.

8. A process according to claim 1 wherein said polymer is a polymer of divinylbenzene.

9. A process according to claim 1 wherein after desorbing the cumene from the mass or bed of said polymer, said cumene is separated from the condensed steam.

10. A process according to claim 1 wherein when cumene is being desorbed from said mass or bed, a cumene containing vapor stream is being passed through at least one additional mass or bed of the substantially dry, hydrophobic, macroreticular, water insoluble crosslinked polymer of claim 1.

* * * * *